(12) United States Patent
Lee et al.

(10) Patent No.: US 6,716,822 B2
(45) Date of Patent: Apr. 6, 2004

(54) THERAPEUTIC AGENT FOR ISCHEMIA WHICH INHIBITS APOPTOSIS UNDER ISCHEMIC CONDITION

(75) Inventors: Jongwon Lee, Taegu (KR); Kyu-Won Kim, Pusan (KR); Jong-Kyun Lee, Seoul (KR); Sang Jong Lee, Seoul (KR)

(73) Assignee: Hypoxi Co., Ltd., Chunchon-shi (KR)

( * ) Notice: Subject to any disclaimer, the term of this patent is extended or adjusted under 35 U.S.C. 154(b) by 0 days.

(21) Appl. No.: 10/181,175

(22) PCT Filed: Jan. 12, 2001

(86) PCT No.: PCT/KR01/00050

§ 371 (c)(1),
(2), (4) Date: Jul. 12, 2002

(87) PCT Pub. No.: WO01/51614

PCT Pub. Date: Jul. 19, 2001

(65) Prior Publication Data

US 2003/0013667 A1 Jan. 16, 2003

(30) Foreign Application Priority Data

Jan. 12, 2000 (KR) .................................. 10-2000-0001309

(51) Int. Cl.$^7$ .................... A61K 31/70; A61K 31/65; A61K 31/497

(52) U.S. Cl. ....................... 514/35; 514/36; 514/37; 514/38; 514/39; 514/40; 514/152; 514/254

(58) Field of Search ................ 514/35, 36, 37, 514/38, 39, 40, 152, 254

(56) References Cited

U.S. PATENT DOCUMENTS

| | | | | |
|---|---|---|---|---|
| 5,532,239 A | * | 7/1996 | Pruna | 514/254 |
| 5,677,288 A | | 10/1997 | Marangos | |
| 5,830,784 A | | 11/1998 | Zhang et al. | |
| 6,180,612 B1 | * | 1/2001 | Hockensmith et al. | 514/25 |
| 6,277,393 B1 | | 8/2001 | Yrjanheikki et al. | |
| 6,281,199 B1 | | 8/2001 | Gupta | |

FOREIGN PATENT DOCUMENTS

| | | |
|---|---|---|
| WO | WO 90/00061 | 1/1990 |
| WO | WO 92/22819 | 12/1992 |

OTHER PUBLICATIONS

Saikku, P., et al. (1988) *Serological Evidence of an Association of a Novel Chlamydia, Twar, with Chronic Coronary Heart Disease and Acute Myocardial Infarction*. Lancet, 2(8618) pp. 983–985.

Gupta, S., et al. (1997) *Elevated Chlamydia Peneumoniae Antibodies, Cardiovascular Events, and Azithromycin in Male Survivors of Myocardial Infarction*. Circulation, 98(2) pp. 404–407.

Muhlestein, JB, et al. (2000) *Radomized Secondary Prevention Trial of Azithromycin in Patients with Coronary Artery Disease: Primary Clinical Results of the ACADEMIC Study*. Circulation, 102(15) pp. 1755–1760.

Gurfinkel, E., et al. (1997) *Randomised Trial of Roxithromycin in Non–Q–Wave Coronary Syndromas: ROXIS Pilot Study*. Lancet, 350(9075) pp. 404–407.

Sinisalo, J., et al. (2002) *Effect of 3 Months of Antimicrobial Treatment with Clarithromycin in Acute Non–Q–Wave Coronary Syndrome*. Circulation, 105(13) pp. 1555–1560.

Folsom, AR. (1999) *Antibiotics for Prevention of Myrocardial Infarction? Not Yet!* JAMA, 281(5) 461–462.

Meier, CR, et al. (1999) *Antibiotics and Risk of Subsequent First–time Acute Myocardial Infarction*. JAMA, 281(5) pp. 427–431.

Haider, AW, et al. (1999) *Letters*, Jama 282(21) 1997–2001.

Hammerschlag, MR. (1994) *Antimicrobial Susceptibility and Therapy of Infections Caused by Chlamydia Pneumoniae*, Antimicrob. Agents Chemother. 38(9) pp. 1873–1878.

Jackson, LA, et al. (1999) *Lack of Association between First Myocardial Infarction and Past Use of Erythromycin, Tetracycline, or Doxycycline*. Emerg. Infect. Disc., 5(2) pp. 281–284.

Luchsinger, JA, et al. (2002) *Relation of Antibiotic Use to Risk of Myocardial Infarction in the General Population*. Am. J. Cardiol. 89(1) pp. 18–21.

Clark, WM, et al. (1994) *Reduction of Central Nervous System Reperfusion Injury in Rabbits Using Doxycycline Treatment*. Stroke 25(7) pp. 1411–1415.

Smith, JR., et al. (1994) *Doxycycline Suppression of Ischemia–Reperfusion–Induced Hepatic Injury*. Inflammation 18(2) pp. 193–201.

Smith, JR., et al. (1995) *Protective Effects of Doxycycline in Mesenteric Ischemia and Reperfusion*. Res. Commun. Mol. Pathol. Pharmacol. 88(3) pp. 303–315.

Yrjanheikki, J., et al. (1998) *Tetracyclines Inhibit Microglial Activation and Are Neuroprotective in Global Brain Ischemia*. Proc. Natl. Acad. Sci. USA 95(26) pp. 15769–15774.

Yrjanheikki, J., et al. (1999) *A Tetracycline Derivative, Minocycline, Reduces Inflammation and protects Against Focal Cerebral Ischemia With a Wide Therapeutic Window*. Proc. Natl. Acad. Sci. USA 96(23) pp. 13496–13500.

(List continued on next page.)

Primary Examiner—Raymond Henley, III
(74) Attorney, Agent, or Firm—Knobbe, Martens Olson & Bear LLP

(57) ABSTRACT

The present invention relates to a therapeutic agent for ischemia which inhibits apoptosis under ischemic condition. The therapeutic agent of the present invention comprises antibacterial agents of quinolones, quinones, aminoglycosides or chloramphenicol as an active ingredient. Since the invented therapeutic agent improved the viability of cells under hypoxic and hypoglycemic condition, it can be clinically for ischemic diseases such as applied as a potential drug for ischemia-associated infarction and cerebral infarction.

5 Claims, 3 Drawing Sheets

OTHER PUBLICATIONS

Chen, M., et al. (2000) *Minocycline Inhibits Caspase–1 and Caspase–3 Expression and Delays Mortality in a Transgenic Mouse Model of Huntington Disease.* Nat. Med., 6(7) 797–801.

Zhu, S., et al. (2002) *Minocycline Inhibits Cytochrome c Release and Delays Progression of Amyotrophic Lateral Sclerosis in Mice.* Nature 417(6884) pp. 74–78.

He, H., et al. (2001) *Phosphorylation of Mitochondrial Elongation Factor Tu in Ischemic Myocardium: Basis for Chloramphenicol–Mediated Cardioprotection.* Circ. Res., 89(5) pp. 461–467.

International Search Report in Application PCT/KR01/00050 completed May 30, 2001.

* cited by examiner

THERAPEUTIC AGENT FOR ISCHEMIA WHICH INHIBITS APOPTOSIS UNDER ISCHEMIC CONDITION

CROSS-REFERENCE TO RELATED APPLICATIONS

This is the U.S. National Phase under 35 U.S.C. §371 of International Application No. PCT/KR01/00050, fired Jan. 12, 2001 and published in English, which claims priority to Korean Application No. 2000/1309, filed Jan. 12, 2000.

BACKGROUND OF THE INVENTION

1. Field of the Invention

The present invention relates to a therapeutic agent for ischemia, more specifically, to a therapeutic agent for ischemia which inhibits apoptosis under ischemic condition.

2. Description of the Prior Art

As the death rate from cardiovascular diseases is increasing recently, researches on the cardiovascular diseases are now in rapid progress. Among them, one of the most noticeable field is that relating to thrombus, wherein efforts to restore blood vessel functions by dissolving thrombus which is the major cause of blockage of blood vessels, and, furthermore, to inhibit thrombus formation are being made. However, there is little progress in developing method for preventing ripple effects of blockage of blood vessels caused by thrombus or other causes. Accordingly, in case of a patient dying of the blockage of blood vessels, it is almost impossible to alleviate ischemic injury which lacks an adequate supply of oxygen and glucose.

It has been reported that administration of antibiotics to the patient who has antibody against *Chlamydia pneumoniae* which is related to onset of acute myocardial infarction reduces the onset rate of acute myocardial infarction(see: Meier C. R. et al., JAMA, 281(5):427–431, 1999). Antibiotics such as quinolones or quinones could reduce onset rate of acute myocardial infarction, on the other hand, antibiotics of macrolide which are known to be the most effective agents to kill *Chlamydia pneumoniae* have no effect on reducing the onset rate of acute myocardial infarction, suggesting that the antibiotics are not merely killing pathogenic microorganisms. Thus, antibiotics have been regarded as thrombosis inhibitors or thrombolytic agents, however, there is no evidence of relations between antibiotics and thrombus, hence, antibiotics can be conjectured to work on acute myocardial infarction via other mechanism than involvement of thrombus. The fact that antibiotics exert a certain effect on acute myocardial infarction without involvement of thrombus implies that antibiotics may protect cells from destruction caused by inadequate supply of oxygen and glucose due to the blockage of blood vessels. Accordingly, it could be expected that the patient who has ischemia due to the blockage of blood vessel can be recovered by using antibiotics, however, there is still little progress in researches of this area.

Under the circumstances, there is a continuing need to understand the mechanism of inhibiting cell damage which is prelude to ischemia and to develop an agent effectively inhibiting the ischemic cell damage.

SUMMARY OF THE INVENTION

The present inventors have made an effort to elucidate the mechanism of inhibiting cell damage which is prelude to ischemia and to develop a therapeutic agent effectively inhibiting the said ischemic cell damage, and, based on the fact that the death of cells under hypoxic and hypoglycemic condition is progressed via apoptosis, they discovered that the addition of antibiotics of quinolones, quinones, aminoglycosides or chloramphenicol to the cells under hypoxic and hypoglycemic condition can dramatically inhibit apoptosis, furthermore, the apoptosis can be inhibited by administering the antibiotics to an individual under ischemic condition in an amount of administering to the individual infected with pathogenic microorganisms.

A primary object of the present invention is, therefore, to provide a therapeutic agent which inhibits apoptosis under ischemic condition.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

Figure 1:
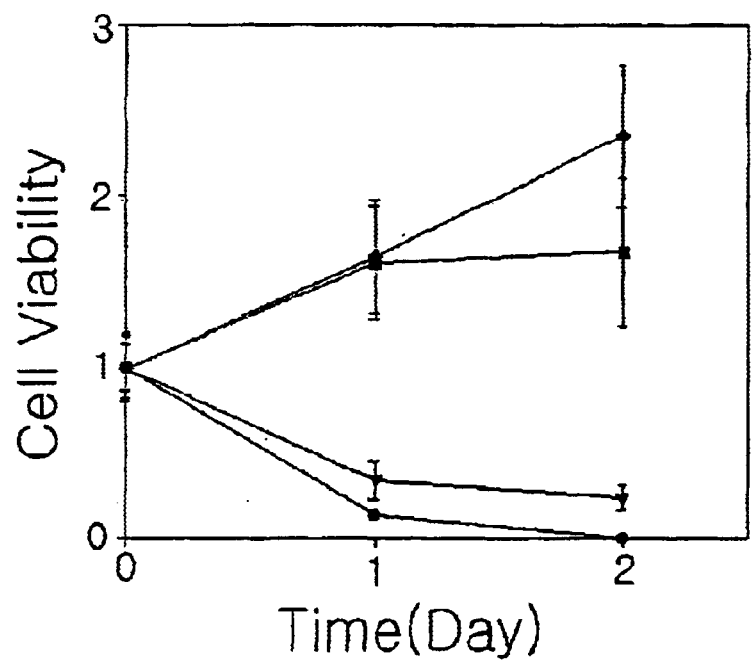
FIG. 1 is a graph showing HepG2 cell viability under various oxygen conditions.

The therapeutic agent of the invention, which inhibits apoptosis under ischemic condition, comprises antibiotics of quinolones, quinones, aminoglycosides or chloramphenicol as active ingredients The present inventors, first of all, examined that apoptosis is induced in cells under ischemic condition which lacks an adequate flow of blood to supply oxygen and glucose due to blockage of blood vessels by thrombus or other causes, and acknowledged that glucose generates energy via TCA cycle and electron transfer system in the presence of oxygen, however, under hypoxic (low oxygen) condition, glucose is converted to lactic acid which generates only a little energy, and resumes energy generation if sufficient oxygen is supplied.

In order to simulate ischemic cells which lack the supply of oxygen and glucose due to the blockage of blood vessels by thrombus or other causes, the present inventors created ischemic condition by discontinuing supply of oxygen and glucose to the cultured cells, and then observed the changes occurred in the cells. When oxygen was depleted in the cells, glucose also became depleted and the cells were died without utilization of lactic acid. When sufficient oxygen was supplied and glucose became depleted, the cells could survive until lactic acid was used up, that is, cells died with exhaustion of lactic acid. However, when cells were treated with antibiotics of quinolones, quinones, aminoglycosides or chloramphenicol, it was found that the cells were viable for a certain period of time even after exhaustion of glucose and production of lactic acid. Preferably, the antibiotics include, but are not intended to be limited to, quinolones of 10–100 μg/ml levofloxacin, 10–100 μg/ml ofloxacin or 1–10 μg/ml ciprofloxacin; quinones of tetracycline, minocycline, doxycycline, or oxytetracycline at a of 0.1–10 μg/ml each; and, aminoglycosides of 10–100 μg/ml geneticin, 500–1000 μg/ml neomycin or 100–1000 μg/ml gentamycin. In case of chloramphenicol, a concentration of 1–10 μg/ml were preferably employed.

Analyses of various test groups of cells under a condition of oxygen and glucose depletion have shown that the groups of cells without antibiotic treatment underwent typical apoptosis, whereas, the groups of cells treated with said antibiotics did not undergo apoptosis for a certain period of time. These results imply that the said antibiotics inhibit apoptosis occurred in cells with ischemic injury which lacks an adequate supply of oxygen and glucose. Additional experiments demonstrated that antibiotics somehow affect the expression of bcl-2 protein which is known to be an inhibitor of apoptosis in cells with ischemic injury.

In order to examine if the results obtained with cultured cells in vitro can be applied to the tissue with ischemic injury, the rats under ischemic condition were treated with the said antibiotics and then hearts from the rats with or without antibiotic treatment were subject to biopsy, and found that the preservation rate of cardiac tissues from rats treated with the antibiotics was higher than that without antibiotic treatment. Accordingly, it was clearly demonstrated that the therapeutic agent comprising active ingredients of antibiotics such as quinolones, quinones, aminoglycosides or chloramphenicol improves the viability of cells under hypoxic and hypoglycemic condition, assuring that it can be clinically applied as a potential drug for ischemia-associated diseases such as myocardial infarction and cerebral infarction.

Considering that most of experimental data using rats intend to apply to mammals and antibiotics employed in the invention are commonly administered to human bodies, the therapeutic agent of the invention, which is prepared on the basis of the experimental results, may be applied to human body to inhibit apoptosis induced under ischemic condition.

The present invention is further illustrated in the following examples, which should not be taken to limit the scope of the invention.

Example 1: Cell viability under various oxygen conditions

HepG2 cells (human hepatoma cell line, ATCC HB 8065, $1\times10^6$ cells/60 mm culture dish) were grown in a minimal essential medium supplemented with 100unit/ml penicillin, 100 μg/ml streptomycin, 1 g/l glucose, 2.2 g/l sodium bicarbonate, and 10% (w/v) fetal calf serum for 2 days, followed by feeding with the same medium and incubating under an environment of 1, 2, or 5% (v/v) oxygen, respectively. Numbers of viable cells with time were determined by trypan blue exclusion assay using hemocytometer after 10–15 minutes of incubation of 1:1 (v/v) mixture of 0.4% (w/v) trypan blue and cell suspension. Cell viability with time was represented in the ratio of viable cell number to cell number just incubation condition was changed to a low oxygen condition(see: FIG. 1). FIG. 1 is a graph showing cell viability under various oxygen conditions, where (●) indicates 1% (v/v), (▼) indicates 2% (v/v), (■) indicates 5% (v/v), and (♦) indicates 21% (v/v) oxygen, respectively. As shown in FIG. 1, it was clearly demonstrated that HepG2 cells were viable in a minimal medium containing low concentration of glucose under an environment over 5% (v/v) oxygen, whereas, the cells died under an environment of less than 2% (v/v) oxygen. Accordingly, a low oxygen condition was set at 1% (v/v) oxygen in the following examples.

Figure 2A:
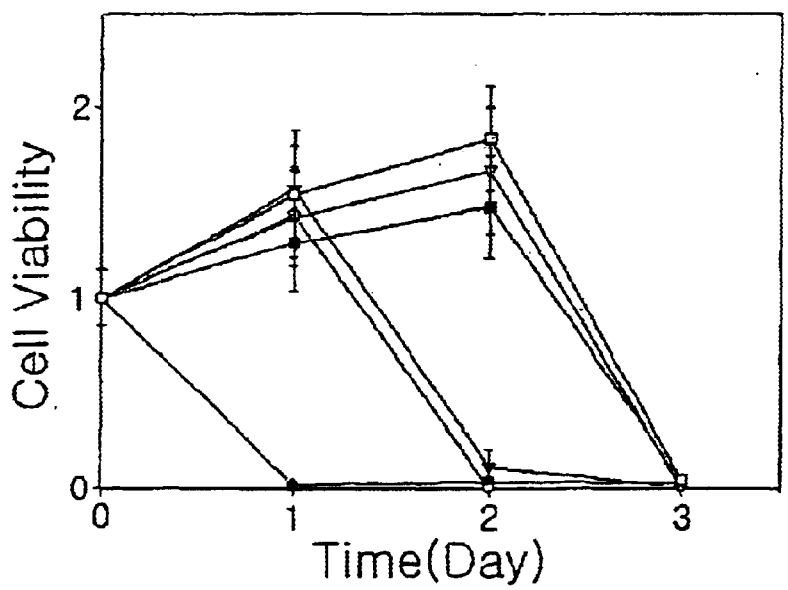
FIG. 2a is a graph showing the dependency of HepG2 cell viability on glucose concentration with incubation time under a low oxygen condition.
Figure 2B:
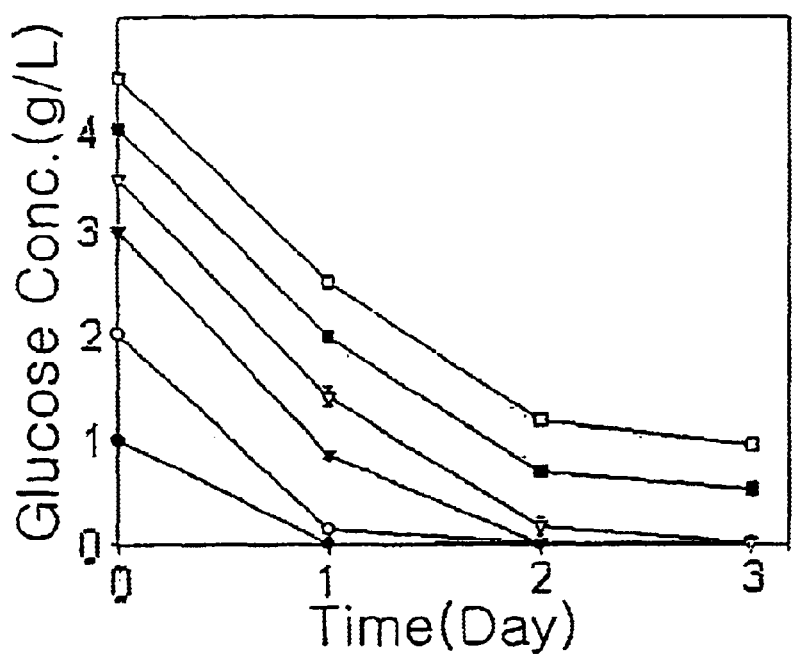
FIG. 2b is a graph showing the change in residual glucose concentration with time depending on initial glucose concentration under a low oxygen condition.
Figure 2C:
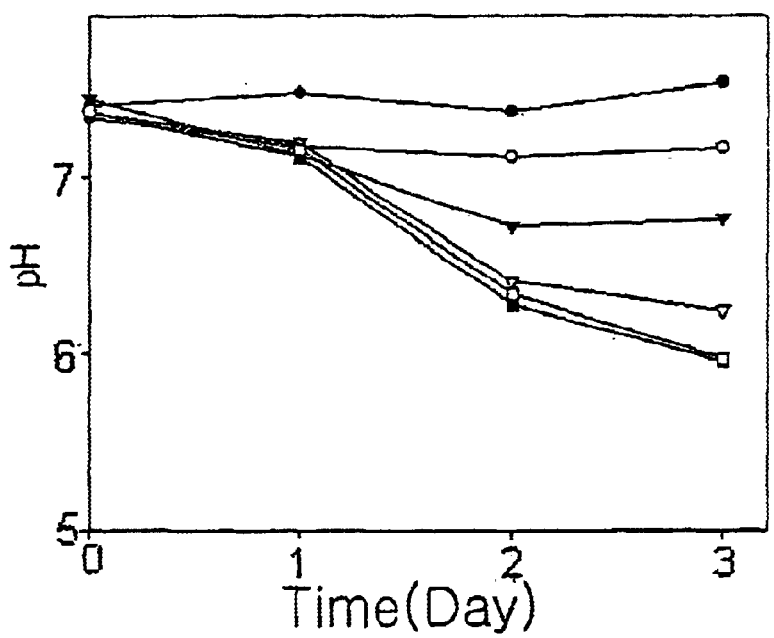
FIG. 2c a graph showing the change in pH with time depending on glucose concentration under a low oxygen condition.

Example 2: Cell viability depending on glucose concentration HepG2 cells were cultured analogously as in Example 1 except for 1% (v/v) oxygen and varied glucose concentrations from 1 to 4.5 g/L. Then, cell viability, changes in glucose concentration and changes in pH with time were measured, respectively(see: FIGS. 2a, 2b and 2c). FIG. 2a shows cell viability with culture time, 2b shows changes in glucose concentration with time, and 2c shows changes in pH with time, where (●) indicates 1 g/L glucose, (○) indicates 2 g/L glucose, (▼) indicates 3 g/L glucose, (▽) indicates 3.5 g/L glucose, (▼) indicates 4 g/L glucose, and (□) indicates 4.5 g/L glucose, respectively. As shown in FIGS. 2a–2c, it was demonstrated that cells were died as a result of depletion of glucose or lowering of pH under a low oxygen condition.

Example 3: Cell viability under various geneticin concentrations

Figure 3:
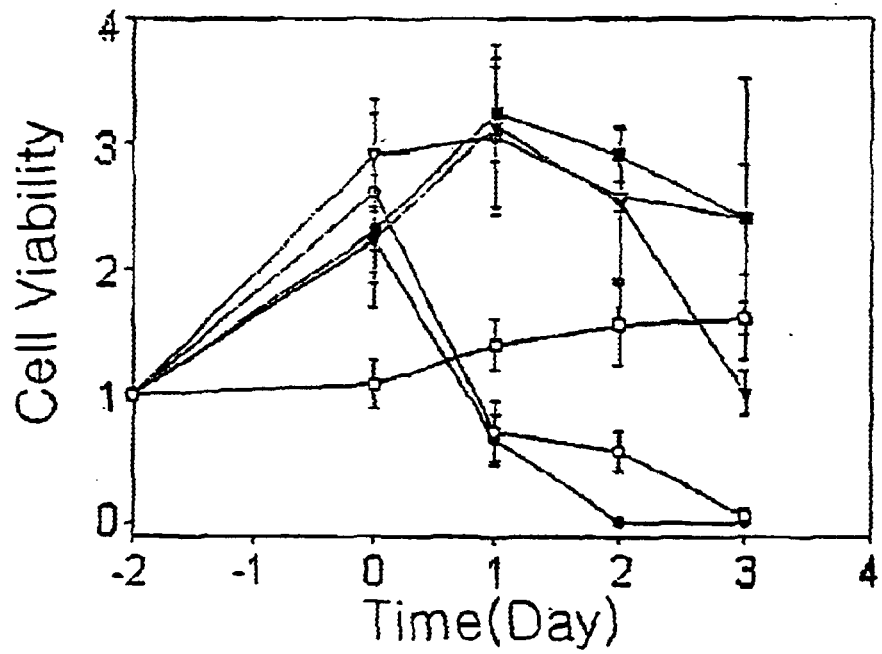
FIG. 3 is a graph showing HepG2 cell viability at various geneticin concentrations.

HepG2 cells were cultured for 2 days in the same manner as in Example 1, and then, the maximum concentration of geneticin at which HepG2 cells can survive was determined by replacing the culture medium with a fresh medium containing 0–1000 μg/ml geneticin, an aminoglycoside antibiotic under an environment of 1%(v/v) oxygen, respectively(see: FIG. 3). FIG. 3 is a graph showing the cell viability at various geneticin concentrations, where geneticin was added at a concentration of 0 μg/ml (●), 1 μg/ml (○), 3 μg/ml (▼), 10 μg/ml (▽), 100 μg/ml (■), and 1000 μg/ ml (□), respectively. As shown in FIG. 3, it was clealy demonstrated that cells treated with 10–100 μg/ml genticin were viable for a certain period of time under an environment of 1% (v/v) oxygen.

Example 4: Effects of various antibiotics on cell viability

Figure 4:
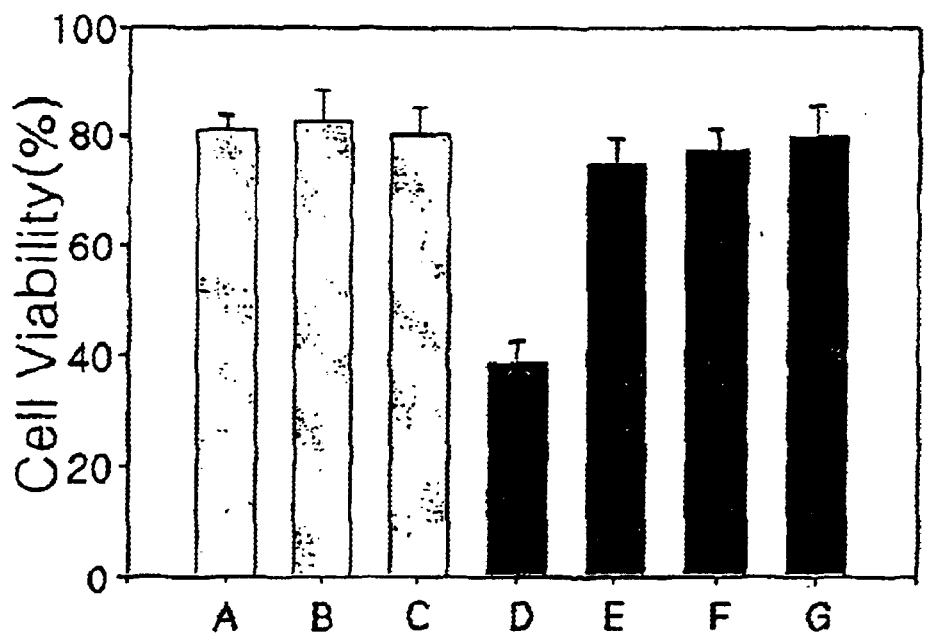
FIG. 4 is a graph showing cell viability of HepG2 treated with various antibiotics.

In order to screen antibiotics which have similar effect to geneticin but have different chemical structure, HepG2 (Human hepatoma cell line, ATCC HB 8065) cells were grown under the same condition described in Example 1, followed by replacing the medium with fresh medium proper for test conditions described below, and then, cell viabilities under various conditions were compared after 2 days of incubation. Test groups were divided as follows depending on test conditions: test group A with 21% (v/v) oxygen and 4.5/L glucose, test group B with 21(v/v) oxygen and 1 g/L glucose, test group C with 1% (v/v) oxygen and 4.5/L glucose, test group D with 1%(v/v) oxygen and 1 g/L glucose, test group E with aminoglycoside antibiotic of geneticin (10 μg/ml) treated test group D, test group F with quinolone antibiotic of ofloxacin test group D, and test group G with antibiotic of doxycycline (0.1 μg/ml) treated test group D (see: FIG. 4). FIG. 4 is a graph showing the comparison of effects of various antibiotics on the cell viability. As shown in FIG. 4, it has been found that: cell viability of test group D was low compared to test groups A, B and C, and cell viability of test group D can be recovered by treatment of various antibiotics.

Example 5: Effect of antibiotics on ischemic cells

Male Sprague-Dawley rats weighing 250 g were injected peritoneally with 45 mg/kg geneticin in test group 1, with 45 mg/kg doxycycline in test group 2, and with 1 cc saline in a conrol group, respectively. Ten rats were included in each test group. After rats were anesthesized by intramuscular injection with 75 mg/kg ketamine and 5 mg/kg xylazine, a tubing was inserted into the airway of the rat and breathing was controlled mechanically at a rate of 70–80 breaths per minute and breathing volume of 15–20 ml/kg. After cutting off the chest bone in the middle, left anterior descending artery (LAD) was ligatured with 6-0 ligature by tying the lower part of the first diagonal branch artery, and the ligature of blood vessel was confirmed by observation of whitening cardiac muscle. Two hours later, blood flow was resumed and 1 cc of Evans blue solution (5%, v/v) was slowly injected into the left ventricle of the heart, and then the heart was removed from the body while leaving the aorta, followed by fixing the heart by using 20 cc of 1% (v/v) triphenyltetrazolium chloride(TTC).

The sections obtained by transverse cutting of the portion from the tip of the heart to right above the ligatured area into 4 equal parts in a 2 mm space were photographed by the aid of flat bad scanner, respectively. The photographs were analyzed and classified into three groups: normal area (Normal) which was stained blue or dark brown, infarct area (Infarct size) which was not stained, and ischemic area(Area at risk) which was stained red. By employing precalibrated image analyzer (Scion Image version 1.62), each stained area was measured. After calculating IS/LV (percentage of infarct area (IS) per cross-sectional area of heart (LV)), and AR/LV (percentage of ischemic area (AR) per cross-sectional area of heart (LV)), IS/(IS+AR)(percentage of infarct area (IS) per sum (IS+AR) of infarct area (IS) and ischemic area was calculated and compared with each other (see: Table 1).

TABLE 1

Effect of antibiotics on ischemic cells (%)

| Test groups | IS/LV | AR/LV | IS/(IS + AR) |
| --- | --- | --- | --- |
| control | 22.7 ± 0.9 | 33.5 ± 2.7 | 40.9 ± 2.5 |
| test group 1 | 12.5 ± 1.8 | 40.0 ± 4.1 | 24.6 ± 2.1 |
| test group 2 | 16.9 ± 2.5 | 41.8 ± 4.3 | 29.3 ± 4.2 |

As shown in Table 1 above, it was found that: infarct area (IS) were reduced in ischemic cells treated with geneticin and doxycycline; and, there were little deviations owing to ligatured artery, in a view that the ratio of normal area ranged 41.3 to 47.5%.

Example 6: Screening of antibiotics exerting effects on cell viability

In order to examine whether antibiotics with other structures than aminoglycoside antibiotic of geneticin, can also enhance cell viability under a hypoxic condition, analyses were performed as followings: i.e., after analysis of antibiotics such as geneticin, neomycin, gentamycin, tetracycline, minocycline, oxytetracycline, doxycycline, chloramphenicol, levofloxacin, ofloxacin, ciprofloxacin, ampicillin, amoxicillin, cephalosporin, erythromycin, suifadiazlne, cyclohexamide, 5-fluorouracil, puromycin and trimetazidine in accordance with the procedure described in Examples 2 and 3, antibiotics which showed enhancement of cell viability under hypoxic condition were selected and their effective concentrations were determined, respectively (see: Table 2).

TABLE 2

Antibiotics exerting enhancement effects on cell viability and their effective concentration

| Antibiotics | Concentration ($\mu$g/ml) |
| --- | --- |
| geneticin | 10–100 |
| neomycin | 1000 |
| gentamicin | 100–1000 |
| tetracycline | 0.1–10 |
| minocycline | 0.1–10 |
| doxycycline | 0.1–10 |

TABLE 2-continued

Antibiotics exerting enhancement effects on cell viability and their effective concentration

| Antibiotics | Concentration ($\mu$g/ml) |
| --- | --- |
| oxytetracycline | 0.1–10 |
| chloramphenicol | 1–10 |
| levofloxacin | 10–100 |
| ofloxacin | 10–100 |
| ciprofloxacin | 1–10 |

Effective concentration ranges in Table 2 represent the concentration ranges of antibiotics exerting enhancement effects on HepG2 cell viability under 1%(v/v) oxygen condition. As shown in Table 2 above, among the antibiotics known to act on 30S subunit of ribosome in E.coli, neomycin and gentamycin other than geneticin were effective among aminoglycoside antibiotics. Also, among the antibiotics known to act on 30S subunit of ribosome in E.coli, a quinone antibiotic of tetracycline was effective at very low concentration range of 0.1–10 $\mu$g/me, and tetracycline derivatives such as minocycline, oxytetracycline and doxycycline were effective at the same range of low concentration. Meanwhile, among the antibiotics known to act on 50S subunit of ribosome in E.coli, an aromatic antibiotic of chloramphenicol was effective, but a macrolide antibiotic of erythromycin was not effective. Among quinolone antibiotics known to act on DNA gyrase, all analyzed compounds, levofloxacin, ofloxacin, and ciprofloxacin were effective. However, antibiotics known to inhibit synthesis of cell wall of microorganisms, such as ampicillin, amoxillin, and cephalosporin did not show enhancement effect on cell viability. Antibiotics such as a sulfadiazine which is known to inhibit dihydropteroate synthetase in the folic acid metabolism, a cyclohexamide inhibiting protein synthesis in eukaryotes, a 5-fluorouracil blocking DNA synthesis by competing with uracil, and a puromycin inhibiting protein synthesis did not show any effect on cell viability. Based on these results, it has been demonstrated that there is no significant relations between the ability of antibiotics to enhance cell viability under hypoxic condition and the action mechanism of antibiotics or the chemical structure of antibiotics. Although efficacy of antibiotics to maintain cell viability under hypoxic condition varies, effective concentration range of antibiotics on enhancement of viability of human hepatoma cell line was about 0.1 to 1000 $\mu$g/ml. Meanwhile, trimetazidine which is known to enhance cell viability by increasing utilization of glucose under a hypoxic condition did not show positive results in the present invention.

Administration Route and Effective Dose

The pharmaceutical compositions comprising antibiotics of quinolones, quinones, aminoglycosides or chloramphenicol as active ingredients and pharmaceutically acceptable carriers can be administered by an injection formula. As the injection formula, isotonic aqueous solution or suspensions are preferred, which are sterilized and/or supplemented with preservatives, stabilizers, wetting agents, emulsifiers, or salts for controlling osmotic pressure and/or buffers. In addition, they may further comprise other therapeutically useful substances.

Upon using the therapeutic agents comprising antibiotics as active ingredients, the antibiotics are administered to an individual in an amount of administering to the individual infected with pathogenic microorganisms. Though the effective dose of an aminoglycoside antibiotic like geneticin is variable depending on the age, body weight of patient and progression of disease, it is preferable to administer parenterally 2 to 3 g/day to an average adult (body weight of 60 kg) in a single dose, which may be individualized by experience of the skilled in the art.

Acute Toxicity Test

All antibiotics used in the present invention, except for an aminoglycoside antibiotic of geneticin, were not subject to acute toxicity tests since they have been clinically approved for their safety. In case of geneticin, after subcutaneously injecting geneticin into male C57BL/6 mice, dead mice were counted through 1–7 days. The results demonstrated that the therapeutic agent comprising geneticin is obviously a safe pharmaceutical drug in an effective dose range, in a view that $LD_{50}$ value is about 3800 mg/kg.

As clearly illustrated and demonstrated above, the present invention provides therapeutic inhibiting apoptosis under ischemic condition, comprise antibiotics of quinolones, quinones, aminoglycosides or chloramphenicol as active ingredients. The therapeutic agents improves the viability of cells under hypoxic and hypoglycemic condition, assuring that they can be clinically applied for ischemia-associated diseases such as myocardial infarction and cerebral infarction, and biotechnology as well.

Various modifications of the invention in addition to those shown and described herein will be apparent to those skilled in the art from the foregoing description. Such modifications are also intended to fall within the scope of the appended claims.

What is claimed is:

1. A method for inhibiting apoptosis under ischemic conditions in an individual in need of such inhibition, the method comprising administering to the individual an effective amount to inhibit apoptosis under ischemic conditions of a composition comprising at least one quinolone antibiotic substance and a pharmaceutically acceptable carrier.

2. The method of claim 1, wherein the quinolone antibiotic substance is selected from the group consisting of levofloxacin, ofloxacin and ciprofloxacin.

3. A method for inhibiting apoptosis under ischemic conditions in an individual in need of such inhibition, the method comprising administering to the individual an effective amount to inhibit apoptosis under ischemic conditions of a composition comprising at least one aminoglycoside antibiotic substance and a pharmaceutically acceptable carrier.

4. The method of claim 1, wherein the at least one aminoglycoside antibiotic substance is selected from the group consisting of geneticin, neomycin and gentamycin.

5. A method for inhibiting apoptosis under ischemic conditions in an individual in need of such inhibition, the method comprising administering to the individual an effective amount to inhibit apoptosis under ischemic conditions of a composition comprising chloramphenicol and a pharmaceutically acceptable carrier.

* * * * *